United States Patent
Horvath et al.

(10) Patent No.: US 9,227,965 B2
(45) Date of Patent: Jan. 5, 2016

(54) PROCESSES AND INTERMEDIATES FOR PREPARING A MACROCYCLIC PROTEASE INHIBITOR OF HCV

(71) Applicant: Janssen Pharmaceuticals, Inc., Titusville, NJ (US)

(72) Inventors: Andras Horvath, Turnhout (BE); Dominique Paul Michel Depré, Hamme-Mille (BE); Dominic John Ormerod, Hoogstraten (BE)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 14/345,980

(22) PCT Filed: Sep. 21, 2012

(86) PCT No.: PCT/EP2012/068593
§ 371 (c)(1),
(2) Date: Mar. 20, 2014

(87) PCT Pub. No.: WO2013/041655
PCT Pub. Date: Mar. 28, 2013

(65) Prior Publication Data
US 2014/0228574 A1    Aug. 14, 2014

(30) Foreign Application Priority Data
Sep. 22, 2011   (EP) .................................... 11182375

(51) Int. Cl.
C07D 453/02    (2006.01)
C07D 453/04    (2006.01)
C07D 311/06    (2006.01)
C07D 417/04    (2006.01)
C07C 235/82    (2006.01)

(52) U.S. Cl.
CPC ............ *C07D 453/02* (2013.01); *C07C 235/82* (2013.01); *C07D 311/06* (2013.01); *C07D 417/04* (2013.01); *C07D 453/04* (2013.01)

(58) Field of Classification Search
None
See application file for complete search history.

(56) References Cited

FOREIGN PATENT DOCUMENTS

| WO | WO 2005/073195 A2 | 8/2005 |
|---|---|---|
| WO | WO 2005/073216 A2 | 8/2005 |
| WO | WO 2007/014926 A1 | 2/2007 |
| WO | WO 2008/092955 A1 | 8/2008 |
| WO | WO 2010/072742 A1 | 7/2010 |
| WO | WO 2011/113859 A1 | 9/2011 |

OTHER PUBLICATIONS

ChiroSolv® Resolving Kits, ChemFiles, ALDRICH CHEMS., (Supplement I) (2008).*
Rosenquist et al., "Synthesis of Enantiomerically Pure trans-3 ,4-Substituted Cyclopentanols by Enzymatic Resolution" Acta Chemica Scandinavica 46 (1992) 1127-1129.
Honda et al., "A Synthesis of (±)-Brefeldin A" Tetrahedron Letters, vol. 22, No. 28, pp. 2679-2682 (1981).
Bartlett et al., "Total Synthesis of Brefeldin A", Journal of the American Chemical Society, American Chemical Society, Washington, D.C. vol. 100, No. 15, pp. 4858-4865 (1978).
Ahlbrecht et al., "Stereoselective Synthesis, EPC Synthesis by Optical Resolution", Methods of Organic Chemistry, Stereoselective Synthesis, pp. 81-101 (1995) XP002594193.
Wen Fei, Deng Yi, Chen Ligong. Use of cyanuric chloride in catalyzing organic syntheses. Speciality Petrochemicals, pp. 71-75, issue 6, vol. 24, Nov. 2007.
Wen Fei, Deng Yi, Chen Ligong. Use of cyanuric chloride in catalyzing organic syntheses. Speciality Petrochemicals, pp. 71-75, issue 6, vol. 24, Nov. 2007. (English Translation).

* cited by examiner

*Primary Examiner* — Timothy R Rozof
(74) *Attorney, Agent, or Firm* — Andrea Jo Kamage

(57) ABSTRACT

Disclosed is a process for the preparation of a cinchonidine salt of formula (IV) via an aqueous solution of a racemic 4-hydroxy-1,2-cyclopentanedicarboxylic acid, which is subjected to cyclization without removing water, by the addition of a water-miscible organic solvent to the aqueous solution and, again without removing water, adding cinchonidine to the aqueous-organic solvent solution so as to obtain the cinchonidine salt of the lactone acid. The cinchonidine salt is allowd to crystallize so as to obtain the enantiomerically purified crystalline lactone acid cinchonidine salt (IV). The enantiomerically pure salt is an intermediate in the synthesis of HCV inhibitor compound of formula (I).

(IV)

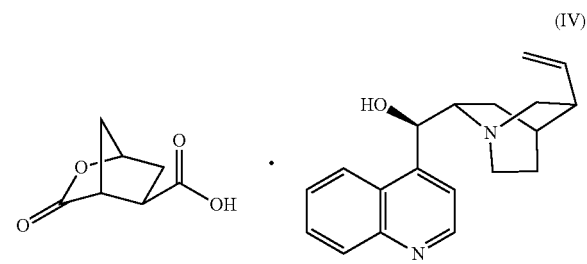

16 Claims, No Drawings

PROCESSES AND INTERMEDIATES FOR PREPARING A MACROCYCLIC PROTEASE INHIBITOR OF HCV

CROSS REFERENCE TO RELATED APPLICATIONS

This application claims priority of the benefits of the filing of PCT Application No. PCT/EP2012/068593, filed Sep. 21, 2012, which claims priority benefit of Application No. EP11182375.3 filed Sep. 22, 2011. The complete disclosures of the aforementioned related patent applications are hereby incorporated herein by reference for all purposes.

FIELD OF THE INVENTION

The present invention relates to synthesis procedures and synthesis intermediates of a macrocyclic protease inhibitor of the hepatitis C virus (HCV).

BACKGROUND OF THE INVENTION

The Hepatitis C Virus (HCV) is the leading cause of chronic hepatitis, which can progress to liver fibrosis leading to cirrhosis, end-stage liver disease, and HCC (hepatocellular carcinoma), making it the leading cause of liver transplantations. Current anti-HCV therapy, based on (pegylated) interferon-alpha (IFN-α) in combination with ribavirin, suffers from limited efficacy, significant side effects, and is poorly tolerated in many patients. This prompted the search for more effective, convenient and better-tolerated therapy.

Replication of the genome of HCV is mediated by a number of enzymes, amongst which is HCV NS3 serine protease and its associated cofactor, NS4A. Various agents that inhibit this enzyme have been described. WO 05/073195 discloses linear and macrocyclic NS3 serine protease inhibitors with a central substituted proline moiety and WO 05/073216 with a central cyclopentane moiety. Amongst these, the macrocyclic derivatives are attractive by their pronounced activity against HCV and attractive pharmacokinetic profile.

WO 2007/014926 describes macrocyclic cyclopentane and proline derivatives including the compound of formula I, with the structure represented hereafter. The compound of formula I is a very effective inhibitor of the HCV serine protease and is particularly attractive in terms of pharmacokinetics. Due to its favourable properties it has been selected as a potential candidate for development as an anti-HCV drug. Consequently there is a need for producing larger quantities of this active ingredient based on processes that provide the product in high yield and with a high degree of purity. WO 2008/092955 describes processes and intermediates to prepare the compound of formula I.

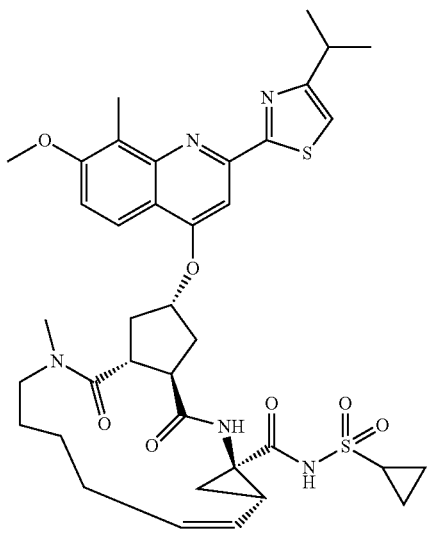

I

According to WO 2007/014926 the compound of formula I can be prepared starting from the bicyclic lactone carboxylic acid referred to as compound 39 in example 4, or in the general description of this reference as compound 17b, or as compound II in this description and claims. The carboxylic acid in bicyclic lactone carboxylic acid is coupled with N-methylhex-5-enylamine 38, followed by lactone opening to 4-hydroxy-cyclopentane derivative 41. The latter derivative 41 is then coupled with aminocyclo-propylcarboxylic ester to cyclopentane dicarboxylic acid diamide 43, which is coupled with quinoline 36 in an Mitsunobu ether-forming reaction, which involves an inversion at the hydroxy-bearing carbon. The resulting intermediate 44 is cyclized via a metathesis reaction to a macrocyclic derivative, in which the ester group is hydrolysed and coupled with cyclopropylsulfonylamide to yield the desired end product of formula I. These reactions are illustrated in the following scheme in which R represents $C_{1-4}$alkyl and in example 4, R is ethyl.

3    4
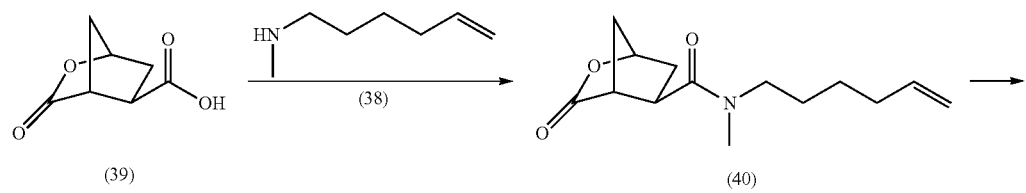
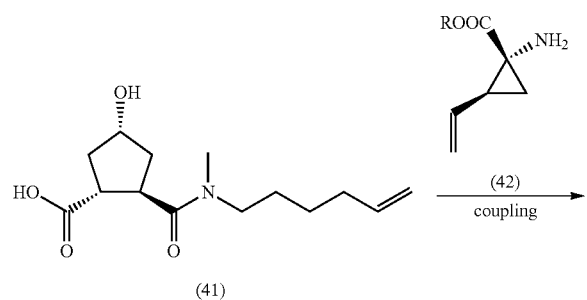
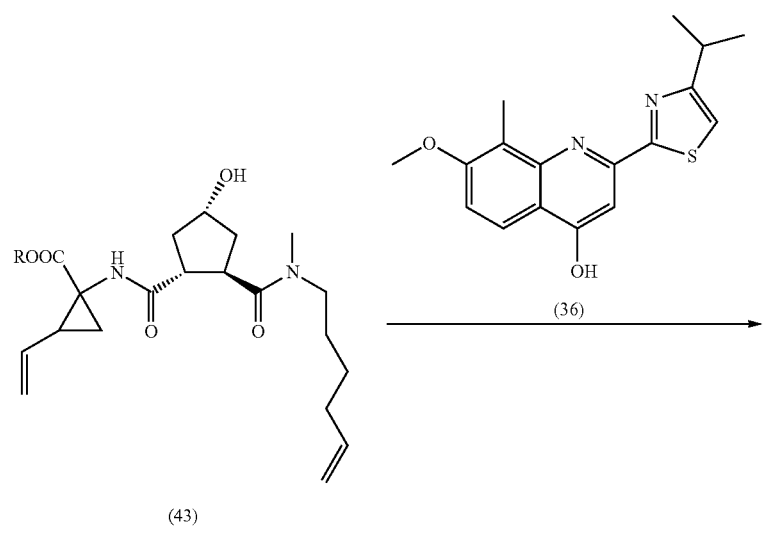

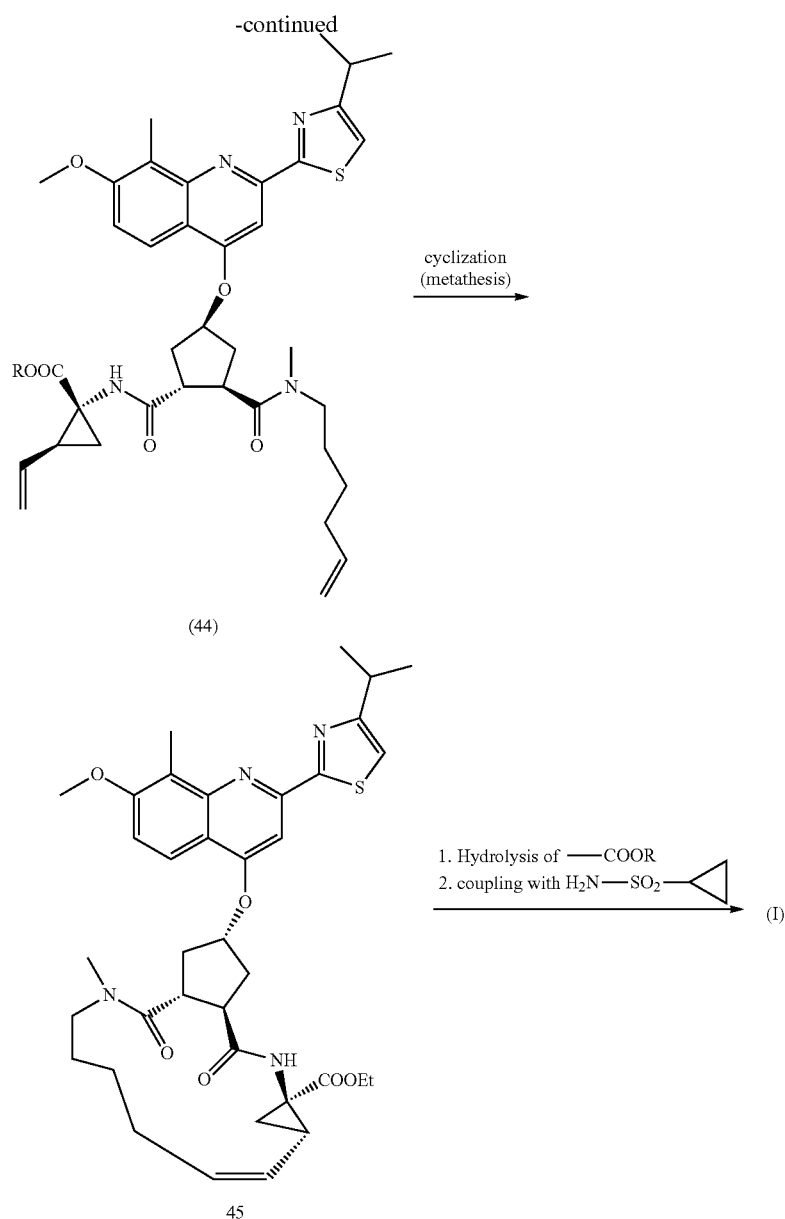

The enantiomercally pure bicyclic lactone 39 was prepared starting from an enantiomer of 3,4-bis(methoxycarbonyl)cyclo-pentanone, referred to as (17a) in WO 2007/014926. The latter was prepared as described by Rosenquist et al. in Acta Chemica Scandinavica 46 (1992) 1127-1129. Racemic cyclohexene dicarboxylic acid methyl ester was synthesized via a Diels-Alder reaction of 3-sulfolene and dimethyl fumarate, followed by oxidative cleavage of the double bond, cyclization, and decarboxylation, resulting in (±) 4-ketocyclopentane dicarboxylic acid dimethyl ester. Resolution of the latter by hydrolysis using pig liver esterase resulted in the corresponding (+)-monoacid and the (−) diester, which is intermediate (17a) of WO 2007/014926.

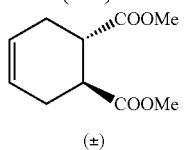

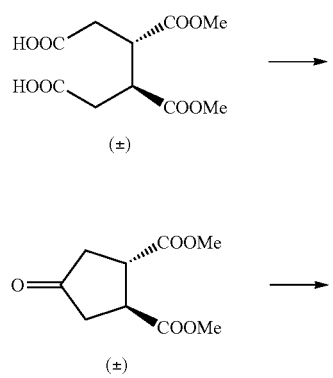

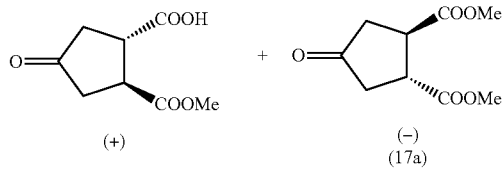

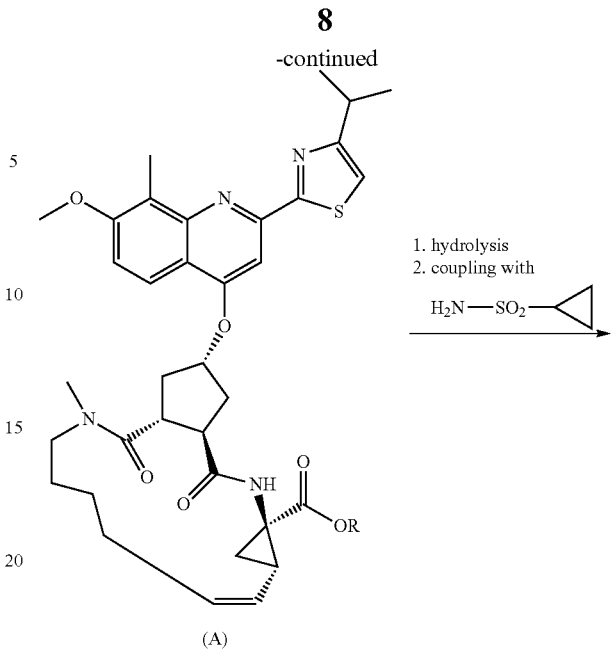

After removal of the (+)-monoacid, the trans (3R,4R)-3,4-bis(methoxycarbonyl) cyclopentanone diester (17a) was converted to the bicyclic lactone 17b (also referred to as compound II, see above), first by a keto to alcohol reduction, followed by hydrolysis of the esters, and lactone formation.

The synthesis procedure for preparing I described in WO 2008/092955 starts from an intermediate D, wherein the ester function is hydrolysed, and coupled with cyclopropyl amino acid ester C. The resulting intermediate B is cyclized by an olefin metathesis reaction to the macrocyclic ester A, which is hydrolyzed and coupled with cyclopropylsulfonylamide to the end product I. These reactions are outlined in the reaction scheme below. In this and the following reaction schemes R is $C_{1-4}$alkyl, in particular R is ethyl. $R^1$ is $C_{1-4}$alkyl, in particular $R^1$ is methyl or ethyl.

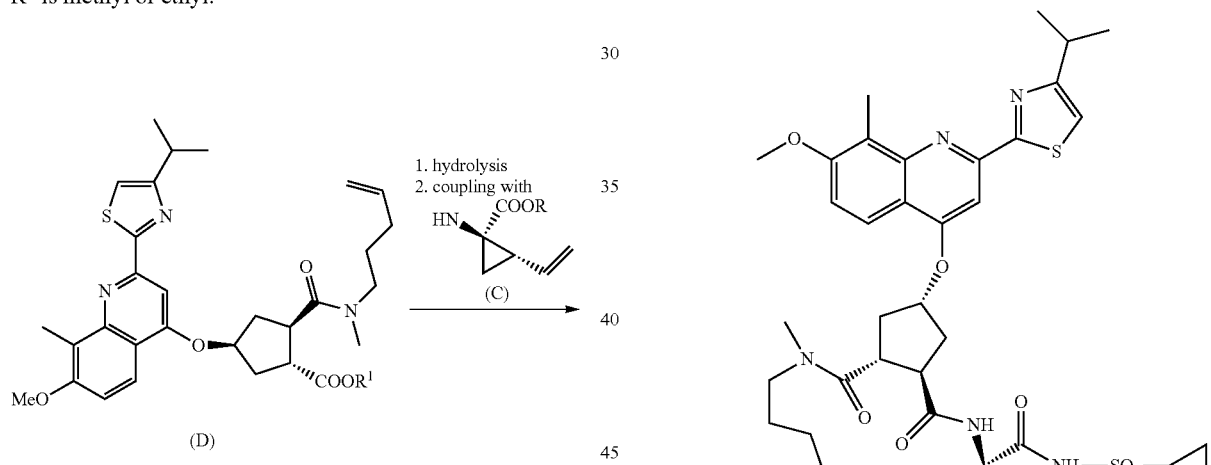

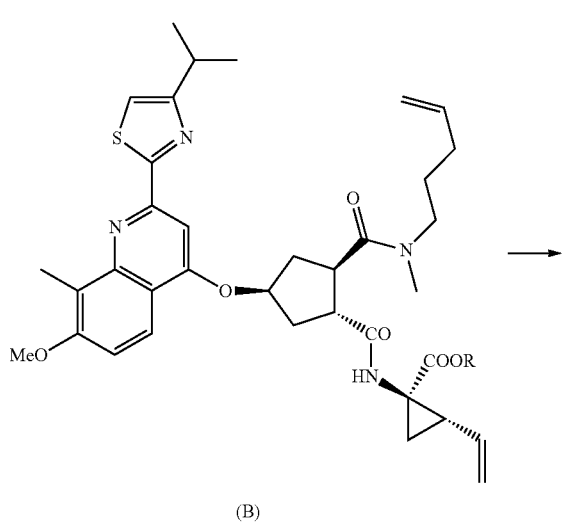

Intermediate D in turn can be prepared starting from a hydroxycyclopentyl bis-ester of formula H1, by either
(a) reacting H1 with a thiazolyl substituted quinolinol E to the quinolinyloxy-cyclopentyl bis-ester of formula K, followed by a cleavage of the benzyl ester group to the mono-carboxylic acid J, which in turn is coupled with an N-methyl hexenamine to intermediate D; or
(b) cleaving the benzyl ester in H1 to the mono-carboxylic acid G, coupling the latter with an N-methyl hexenamine to the hydroxycyclopentylamide F, which in turn is reacted with E, thus obtaining D; as outlined in the following reaction scheme:

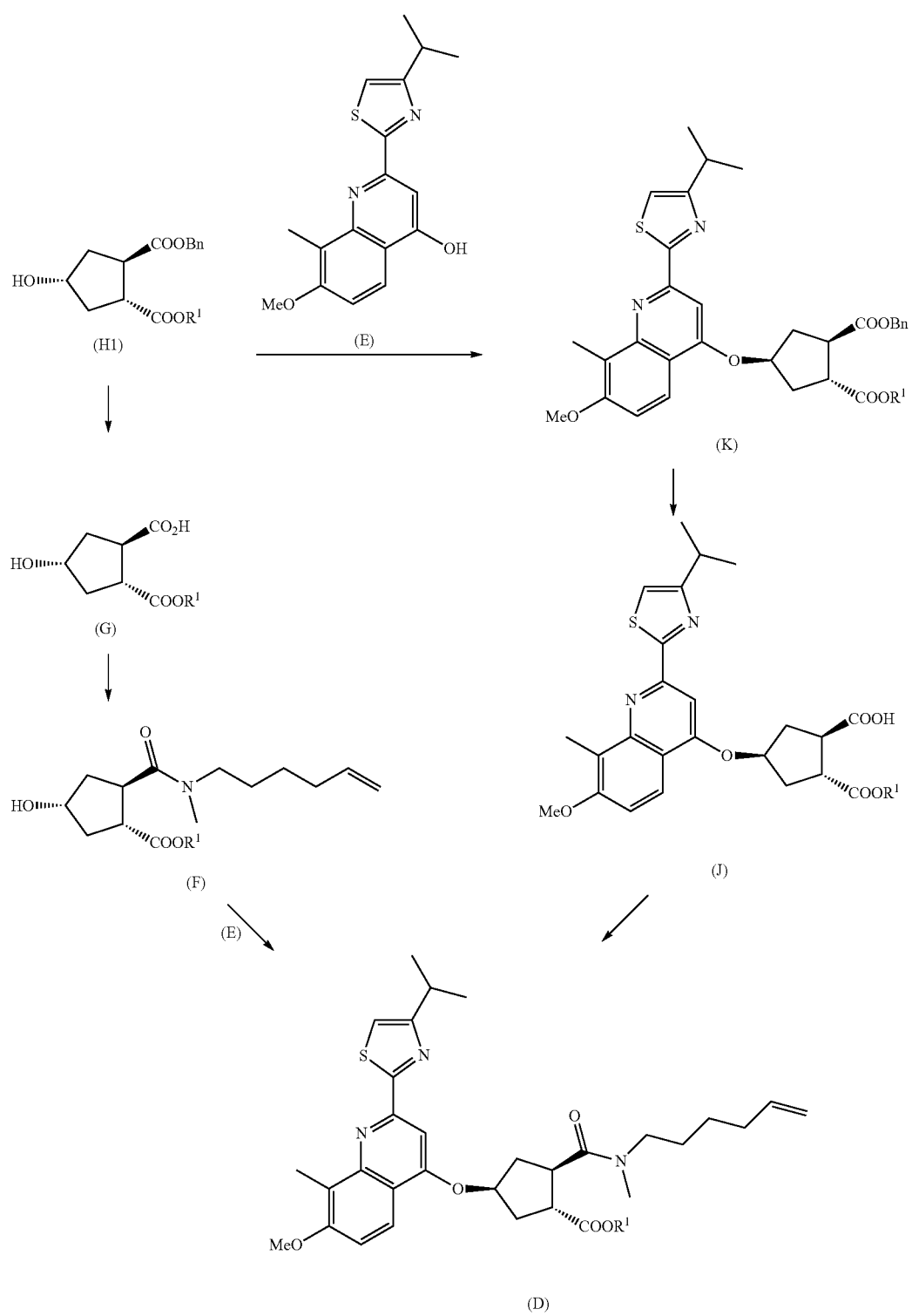

Each $R^1$ is in this scheme is as specified above and Bn represents benzyl.

WO 2008/092955 furthermore describes procedures for preparing intermediate H1 starting from 4-oxo-1,2,-cyclopentanedicarboxylic acid O, by a keto to alcohol reduction, thus obtaining 4-hydroxy-1,2-cyclopentanedicarboxylic acid N, which in turn is cyclized to the bicyclic lactone M. Esterification of the carboxylic acid group in the latter yields the lactone benzyl ester L, wherein the lactone is opened by a transesterification reaction in the presence of a $C_{1-4}$alkanol, thus yielding intermediate H, which is resolved in its enantiomers H1 and H2, as outlined in the following reaction scheme:

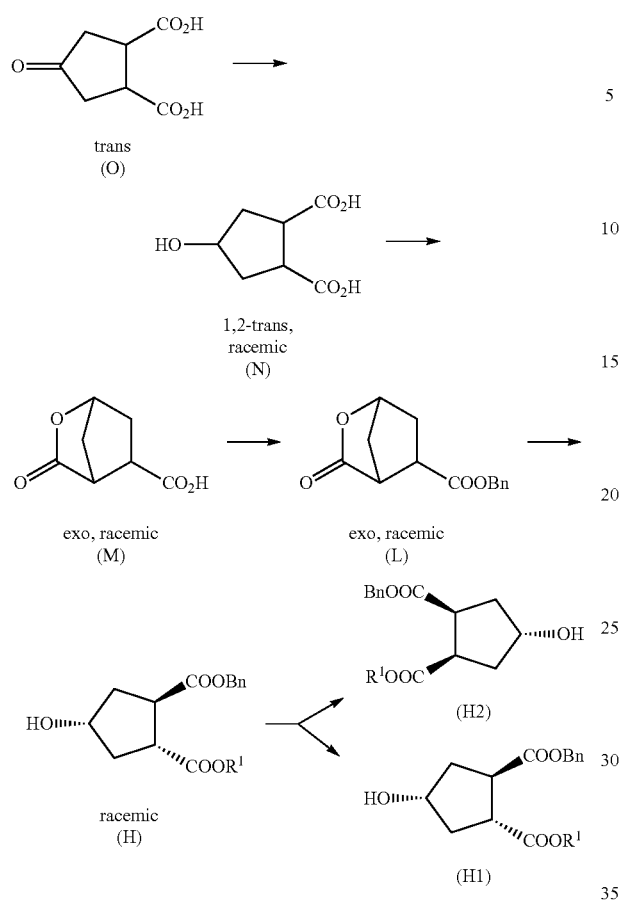

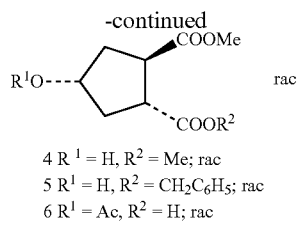

4 R¹ = H, R² = Me; rac
5 R¹ = H, R² = CH₂C₆H₅; rac
6 R¹ = Ac, R² = H; rac

The synthesis of Honda et al. starts from dl-trans-4-oxo-cyclopentane-1,2-dicarboxylic acid 2, which was esterified to the corresponding methyl ester 3, and reduced with Raney-Ni to the alcohol 4. Partial hydrolysis of 4 to the monocarboxylic acid and benzylation with benzyl bromide gave predominantly diastereoisomer 5, namely the diastereoisomer wherein the hydroxy and benzyl ester groups are in cis position. The latter ester 5 in Honda et al. and compound H are both racemates, but are diastereoisomers of one another, more precisely epimers on the carbon no. 4 bearing the hydroxy group. Compound H1 is one of the two enantiomers obtained by separation from the racemic compound H. The other enantiomer is compound H2.

The bicyclic lactone (17b) is an interesting building block in the synthesis of the compound of formula I. Finding a synthesis path to obtain this lactone in good yield and high enantiomeric purity is a desirable goal to achieve. The present invention provides such a process.

WO 2010/072742 describes the use of the cinchonidine salt of the aforementioned bicyclic lactone as an intermediate in the preparation of intermediate (IX), and therefore also in the preparation of the HCV inhibitor (I).

A disadvantage of the above process is that it involves a resolution of the enantiomers of H by chiral column chromatography, a cumbersome procedure that is difficult to run at large scale production. Another disadvantage is that the resolution takes place at a later stage of the synthesis, whereby half of the building block H has to be discarded. The presence of various chiral centers in the compound of formula I and its predecessors poses particular challenges in that enantiomeric purity is essential to have a product that is acceptable for therapeutic use. Hence the processes for preparing D should result in products of acceptable enantiomeric purity without use of cumbersome purification procedures with the loss of substantial amounts of undesired stereoisomeric forms.

Honda et al. Tetrahedron Letters, vol. 22, no. 28, pp 2679-2682, 1981, describes the synthesis of (±)-brefeldin A, using the following starting materials:

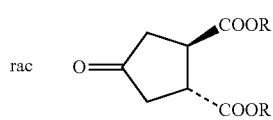

2 R = H; rac
3 R = Me; rac

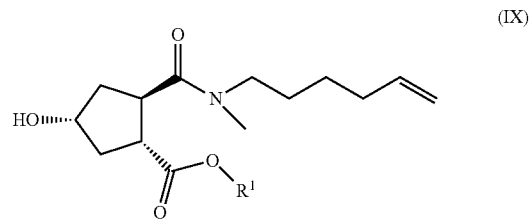

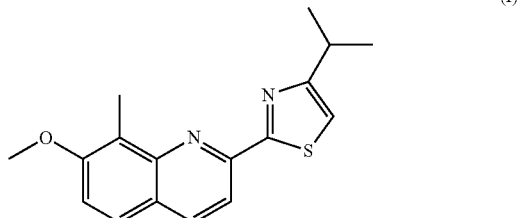

In WO 2010/072742, the cinchonidine salt (IV) is prepared via the resolution of a diastereoisomeric salt mixture (III) by selective crystallization. The salt (III) in turn is obtained by forming the cinchonidine salt of the racemic bicyclic lactone carboxylic acid (II), as outlined in the following reaction scheme:

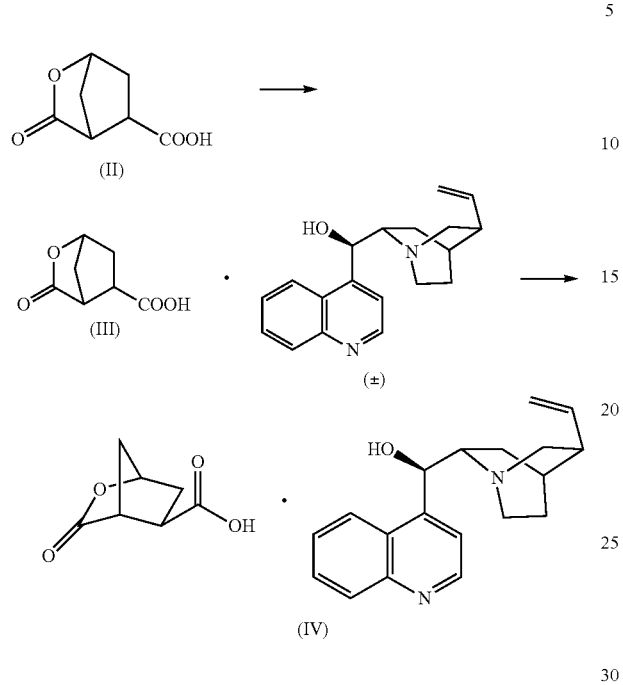

It is desired to provide a more convenient process for preparing the cinchonidine salt (IV).

SUMMARY OF THE INVENTION

The invention, in one aspect, provides a process for the preparation of a cinchonidine salt of formula (IV) comprising the steps of:

(a) subjecting 4-oxo-1,2-cyclopentanedicarboxylic acid (V) to reduction in an aqueous environment, thus providing an aqueous solution of racemic 4-hydroxy-1,2-cyclopentanedicarboxylic acid (VI);

(b) adding an organic solvent (e.g. a water-miscible organic solvent) to the aqueous solution obtained in (a);

(c) subjecting the racemic hydroxyacid (VI) to cyclization so as to obtain an aqueous-organic solvent solution of the corresponding racemic lactone acid (II);

(d) adding cinchonidine to the aqueous-organic solvent solution obtained in (c) so as to obtain the cinchonidine salt (III) of the lactone acid;

(e) allowing the cinchonidine salt to crystallize so as to obtain the enantiomerically purified crystalline lactone acid cinchonidine salt (IV), the numbered formulae herein being as follows:

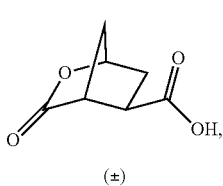

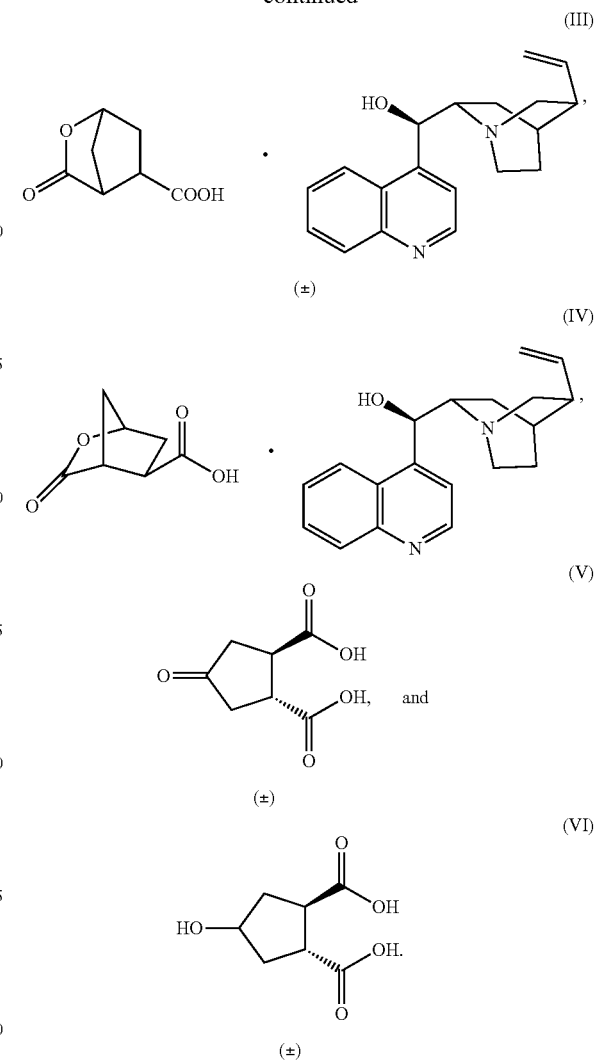

For instance, in an aspect of the invention, the steps (a), (b) and (c) are performed (not necessarily followed by steps (d) and (e)), although preferably all steps (a) to (e) are performed consecutively. In a further aspect, steps (d) and (e) are performed, which are not necessarily preceded by all of steps (a), (b) and (c) (although they preferably are).

The compounds employed in the processes described herein (e.g. compounds of formula (V), (VI) and (II), as well as other compounds, e.g. involved in the downstream chemistry in the synthesis of the HCV inhibitor compound of formula I or salt thereof) may be in the non-salt forms or they may be in the salt forms. For instance, the compound of formula (VI) may exist in a salt form when employed in the processes described herein, e.g. it may exist as a bis-salt, wherein the salt is for instance an inorganic metal e.g. Na or K (or the like) or the salt is an amine (e.g. an organic amine such as triethylamine or N-methylmorpholine, or the like). Examples of formula (VI) include the bis-potassium salt and the bis-triethylamine salt. Of course, when the salt of formula (VI) is in an aqueous solution, there may be dis-association (to a certain degree).

Hence, there is provided a process for the preparation of a racemic lactone of formula (II), which process comprises intramolecular cyclization of a compound of formula (VI)

(also a racemic mixture), characterised in that the reaction is performed in the presence of water (see step (c) described herein). As stated herein, the compound of formula (VI) may be employed in the form of a salt (e.g. a bis-salt). Such a reaction may conveniently be preceded by a reaction that is performed in the presence of water, e.g. the reduction of racemic compound (V) to racemic compound (VI) (see step (a) described herein). As stated herein, step (a) may be performed in the presence of a base and hence the compound of formula (VI) may form a salt with the base employed (e.g. Na, K, triethylamine, N-methylmorpholine or diisopropylethylamine). However, given that this step is performed in the presence of water, any association between (VI) and the counterion (i.e. "salt") may be minimal, in water. Conveniently, any salt of (VI) formed (or any non-salt form of (VI)) need not be isolated or purified in subsequent steps, given that the process described hereinbefore for preparing the lactone (II) is characterised in that it is performed in the presence of water. Optionally, after the reduction reaction to form (VI) an organic solvent (e.g. water-miscible organic solvent) is added (see step (b) described hereinbefore) as described herein, i.e. in the step immediately preceding the lactone-forming step to produce (II). It is advantageous that the lactone-forming step can be performed in water, especially since water is formed as a by-product of the reaction and hence it is surprising that the reaction proceeds as described herein. Advantageously, water that is employed in reaction steps need not be removed for subsequent reaction steps (e.g. between the step (V) to (VI) and the step (VI) to (II), or, between the step (VI) to (II) and step (II) to (III) to (IV).

In another aspect, there is provided a process for the preparation of a cinchonidine salt of formula (III) or (IV) (i.e. the racemic, or, preferably, the enantiomerically pure salt), which process comprises contacting cinchonidine with racemic lactone acid (II), characterised in that the reaction is performed in the presence of water. The reaction may also be performed in the presence of water mixed with an organic solvent, and hence this reaction may conveniently directly proceed the processes described herein for the preparation of the lactone acid (II).

In another aspect, the invention provides a process for the preparation of an intermediate (IX) for the preparation of a HCV inhibitor compound of formula I, the process comprising the steps of preparing an enantiomerically purified crystalline lactone acid cinchonidine salt (IV) in a process comprising the described hereinbefore (e.g. steps (a) thru (e) as identified above or also the other processes described herein for the preparation of (IV)), and reacting the lactone acid cinchonidine salt (IV) with N-methyl-hexenamine (NMHA) (VII) in an amide-forming reaction to yield the bicyclic lactone amide (VIII), in which the lactone group is opened to yield the desired product (IX), as illustrated in the scheme below, wherein $R^1$ is $C_{1-4}$alkyl:

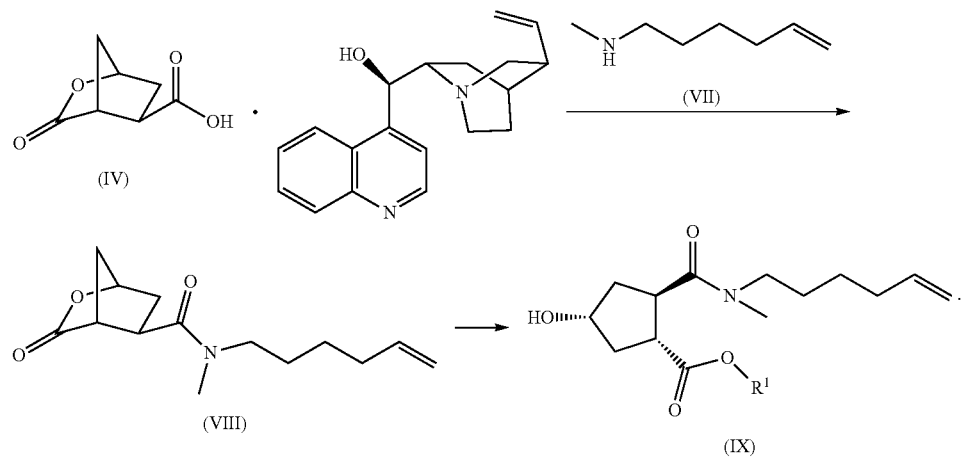

In yet another aspect, the invention provides a process for the preparation of compound (I) comprising preparing the cinchonidine salt as described above, followed by preparing compound IX as described above, and using compound (IX) as an intermediate in the synthesis of (I).

DESCRIPTION OF THE INVENTION

Overview of structures described in this description and claims.

| Compound number | Structure |
|---|---|
| I | 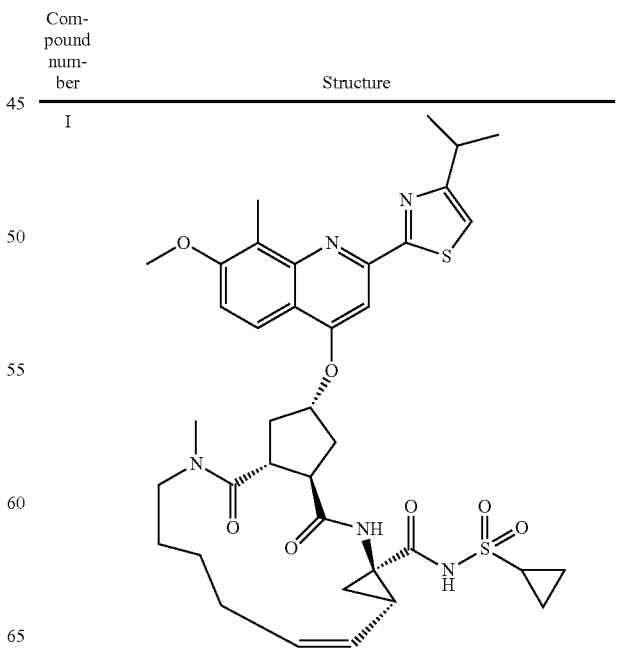 |

-continued

| Compound number | Structure |
|---|---|
| II | (structure) identical with (structure) (±) |
| III | (structure) (III) (±) |
| IV | (structure) (±) |
| V | (structure) (±) |
| VI | (structure) (±) |
| VII | (structure) |
| VIII | (structure) |

-continued

| Compound number | Structure |
|---|---|
| IX | 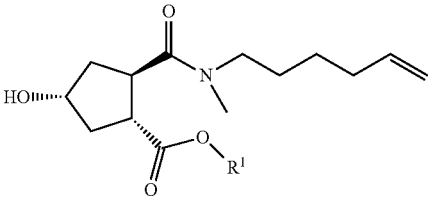 |

The process of the invention starts with providing the 4-oxo-1,2-cyclopentanedicarboxylic acid (V). The racemic 4-oxo-1,2-cyclopentanedicarboxylic acid V starting material can be prepared as described above in the Background of the Invention section.

The keto acid (V) is subjected to reduction in an aqueous environment, thus providing an aqueous solution of racemic 4-hydroxy-1,2-cyclopentanedicarboxylic acid (VI). The keto to hydroxy reduction to convert V into VI can be done using a suitable reductant, in particular by hydrogen in the presence of a metal catalyst, e.g. rhodium on carbon or on alumina or Raney Ni, in a reaction-inert solvent, e.g. in an aqueous medium, such as water, in the presence of a base, e.g. NaOH, KOH, or an organic base such as triethylamine, N-methylmorpholine or Hunig's base (diisopropylethylamine). Hence, the reaction is performed in the presence of water and the product (VI) is obtained in the presence of water (wherein (VI) is optionally in the form of a salt).

The process of the invention brings about the advantage that the sequence of process steps can be conducted without the need for removal of water, salt-formation, precipitation, or other isolation techniques in between. Thus, to the aqueous solution obtained from the aforementioned keto to hydroxy reduction, an organic co-solvent (e.g. a water-miscible organic co-solvent) is added. The skilled person will understand that the organic co-solvent should be inert towards the reaction conducted, and should be (e.g. when it is a water-miscible organic co-solvent) sufficiently water-miscible so as to form a single phase solvent system. However, the solvent system need not necessarily be a single phase solvent system (e.g. a homogenous mixture) but it may be a biphasic (e.g. heterogenous) solvent system. Suitable water-miscible organic co-solvents include ketones, such as acetone or methylethylketone (MEK), ethers, such as tetrahydrofuran (THF) or 2-methyltetrahydrofuran (MeTHF), or acetonitrile. The preferred solvent in this step is acetone. Other solvents that may be mentioned are not necessarily water-miscible, for instance they may be non water-miscible or at least only moderately water-miscible, e.g. an aromatic solvent such as toluene or benzene.

The thus formed racemic hydroxyacid (VI), which is present in solution in the aqueous-organic solvent mixture, is subjected to cyclization, so as to obtain an aqueous-organic solvent solution of the corresponding racemic lactone acid (II). The cyclization can be conducted with known lactone-forming agents (or those mentioned herein, e.g. triazines), such as a chloroformate, e.g. with ethyl or methyl chloroformate. A base can be added, e.g. a tertiary amine such as triethylamine or N-methylmorpholine (NMM). In a preferred embodiment the lactone-forming agent is a triazine, more preferably 2,4,6-trichloro-1,3,5-triazine (TCT) or a derivative thereof.

As an advantage of the process of the invention, preferably using a triazine derivative, the cyclization is conducted in a one-pot procedure without isolation of intermediary products. Triazine derivatives for this reaction comprise agents such as 2,4,6-trichloro-1,3,5-triazine (TCT), chlorodimethoxytriazine (CDMT), N-(3,5-dimethoxytriazinyl)-N-methylmorpholinium chloride (DMTMM) or dichloro-methoxytriazine (DCMT). This reaction sequence offers a simple, short and economical procedure to prepare the racemic lactone acid II in high yield. The water used as solvent in the reduction step need not removed and no separation of the intermediate 4-hydroxy-1,2-cyclopentanedicarboxylic acid VI is necessary.

In order to attain enantiomeric purity, cinchonidine is added. Advantageously, in the process of the invention, this goes without the need to isolate the intermediate lactone acid (II). Thus, cinchonidine is added to the aqueous-organic solvent solution of the lactone acid (II), so as to obtain the cinchonidine salt (III) thereof. In accordance with WO 2010/ 072742, the enantiomerically pure cinchonidine salt (IV) can be isolated by crystallization, which provides an elegant way to resolve the stereochemistry of the bicyclic lactone acid (II), so as to obtain the desired lactone acid in high enantiomeric purity. Recrystallization or reslurrying allows further purification of this salt.

The invention further provides a process for the preparation of an intermediate (IX) for the preparation of a HCV inhibitor compound of formula I. This process first comprises the steps of preparing an enantiomerically purified crystalline lactone acid cinchonidine salt (IV) as described above. Thereupon, the lactone acid cinchonidine salt (IV) is further reacted as described in WO 2010/072742.

This preferably entails the reaction of the lactone acid cinchonidine salt (IV) with N-methyl-hexenamine (NMHA) (VII) in an amide-forming reaction to yield the bicyclic lactone amide (VIII). Therein the lactone group is opened to yield the desired product (IX), as illustrated in the scheme below, wherein $R^1$ is $C_{1-4}$alkyl, and preferably methyl:

such as tetrahydrofuran (THF) or 2-methyltetrahydrofuran (MeTHF), alcohols such as methanol or ethanol, hydrocarbon solvents such as toluene or xylene, dipolar aprotic solvents such as DMF, DMA, acetonitrile, or mixtures thereof. Preferred are dichloromethane, MeTHF, methanol, ethanol, toluene, or mixtures thereof. Amide-coupling agents comprise agents such as N-ethoxycarbonyl-2-ethoxy-1,2-dihydroquinoline (EEDQ), N-isopropoxycarbonyl-2-isopropoxy-1, 2-dihydroquinoline, in particular its hydrochloride salt, (IIDQ), N,N,N',N'-tetramethyl-O-(7-azabenzotriazol-1-yl) uronium hexafluorophosphate (HATU), benzotriazol-1-yl-oxy-tris-pyrrolidino-phosphonium hexafluorophosphate (commercially available as PyBOP®), 1,1'-Carbonyldiimidazole (CDI), 1-ethyl-3-(3-dimethylaminopropyl) carbodiimide (EDI or EDCI) as well as its hydrochloride salt, dicyclohexyl-carbodiimide (DCC), or 1,3-diisopropylcarbodiimide, O-benzotriazole-N,N,N',N'-tetramethyl-uronium-hexafluoro-phosphate (HBTU) and the like. A catalyst may be added, for example 1-hydroxybenzotriazole (HOBt) or 4-dimethylaminopyridine (DMAP). The reaction is usually conducted in the presence of a base, in particular an amine base such as a tertiary amine, e.g. triethylamine, N-methylmorpholine, N,N-diisopropylethylamine, (the latter also being referred to as Hünig's base, DIPEA, or DIEA). Preferably, no base is used. In one embodiment, the reaction is conducted in DCM or MeTHF with EEDQ, optionally with addition of methanol at the end of the reaction, at reflux temperature of the reaction mixture.

In an alternative embodiment, the salt (IV) can be split into cinchonidine and the bicyclic lactone, and the latter can be reacted with NMHA in an amide forming reaction as described above. In accordance with WO 2010/072742, it is advantageous to use the cinchonidine salt (IV) itself in the amide forming reaction, and to thereafter remove the cinchonidine. This removal can be effected easily in the work-up of the reaction mixture, for example by treatment of the latter with an acid such as HCl, and washing away the side products with aqueous phases.

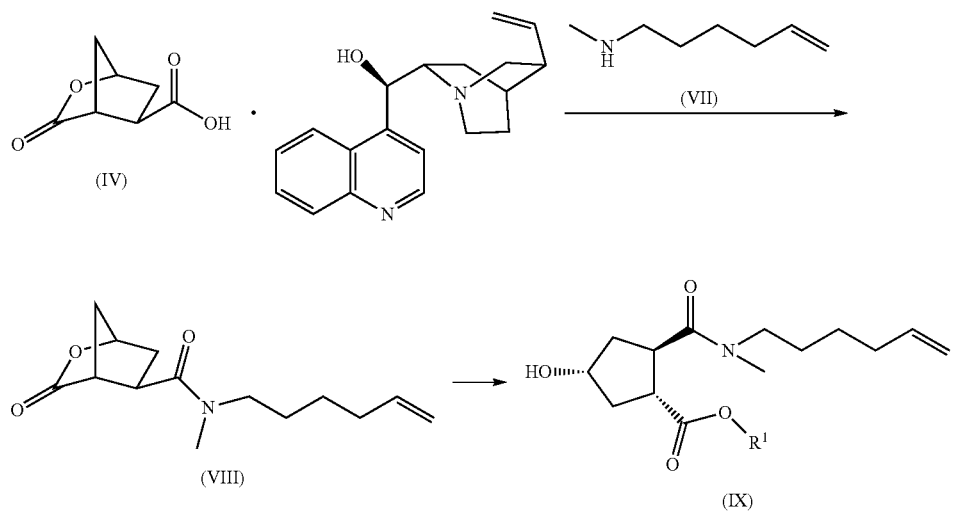

The reaction of the cinchonidine salt (IV) with NMHA (VII) is an amide forming reaction, which comprises reacting the starting materials with an amide-coupling reagent in a reaction-inert solvent, optionally in the presence of a base. Solvents that can be used comprise halogenated hydrocarbons such as dichloromethane (DCM) or chloroform, ethers The lactone functionality in the resulting bicyclic lactone amide (VIII) is opened by a transesterification reaction with an alcohol, which may also serve as a solvent, in particular a $C_{1-4}$alkanol such as methanol or ethanol, in the presence of an acid. Acids that can be used are strong organic acids such as sulfonic acids, in particular methanesulfonic acid. A solvent can be added such as an ether, in particular THF or MeTHF; or hydrocarbon solvents such as toluene or xylene. The transesterification reaction yields the ester of the alcohol that is used, e.g. when conducting the reaction in methanol, the methyl ester is formed.

The resulting compounds (VIII), with $R^1$ preferably being methyl, find use in the procedures to prepare the compound of formula (I).

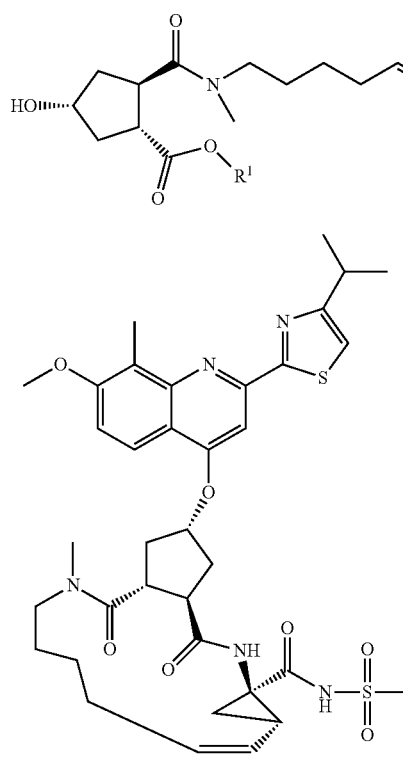

(VIII)

(I)

The further processing of the compound of formula VIII to the end products of formula I are as outlined in the reaction schemes above and in particular as described in WO2008/092955.

The synthesis procedures of the present invention offers the advantage that the correct stereochemistry at the cyclopentane moiety is obtained without using chiral chromatography, and in a process that avoids the isolation of intermediates.

As used in the foregoing and hereinafter, the following definitions apply unless otherwise noted. The term "$C_{1-4}$ alkyl" defines straight or branched chain saturated hydrocarbon radicals having from 1 to 4 carbon atoms such as for example methyl and ethyl; and also 1-propyl, 2-propyl, 1-butyl, 2-butyl, 2-methyl-1-propyl, 2-methyl-2-propyl.

The generally accepted convention for representing stereochemical compounds, which is also adhered to herein is the following:

A compound represented without stereobonds, is racemic or the configuration of the stereogenic center(s) is not defined.

A compound represented with stereobonds and one of the descriptors "(±)", "rel", or "rac", is racemic and the stereochemistry is relative.

A compound represented with stereobonds but without the descriptors "(±)", "rel", or "rac" refers to a non-racemic compound (scalemic substance) i.e. enantio-enriched.

For instance, in the Honda et al. reference the designation "(±)" is used in the title of the article, meaning that there is described a racemic synthesis with racemic intermediates. However the above convention may not necessarily be followed in all publications.

The enantiomeric purity is given as enantiomeric ratio (e.r.). For the salts, the e.r. value refers to the ratio of the two enantiomers of the acid in the mixture of diastereomeric salts.

EXAMPLES

The following examples are intended to illustrate the present invention and should not be construed as a limitation of the scope of the present invention.

Example 1

To a suspension of 32.7 g (0.19 mol) of racemic 4-oxo-1, 2-cyclopentanedicarboxylic acid (intermediate V) in 237.5 ml water under an atmosphere of nitrogen is added 1.0 ml (0.019 mol) 50% wt/wt aqueous NaOH. The mixture is warmed to 60° C. and 2.5 g Rh/C (5% wt/wt) are added. Then the reaction flask is purged with hydrogen and kept under an atmosphere of hydrogen while stirring until complete conversion is reached. The warm reaction mixture is filtered over Celite and the filter cake washed twice with 10 ml water. Triethylamine (55.61 ml, 0.40 mol) is added and 80% of the solvent volume is distilled off under a pressure of 30 mbar. The reaction flask was fitted with a Dean-Stark trap filled with 2-methyltetrahydrofuran. 2-Methyltetrahydrofuran (100 ml) is added to the reaction mixture. The mixture was refluxed for 4 hours to remove the remaining water. Then 80% of the solvent volume is distilled off under ambient pressure. The mixture is cooled to 50° C. and acetone (380 ml) is added. The mixture is cooled further to 22° C. and additional acetone (760 ml) is added. The resulting suspension is cooled under an atmosphere of nitrogen to −5° C. and triethylamine added (27.8 ml, 20.24 g, 0.2 mol). Subsequently, ethyl chloroformate (22.68 g, 0.21 mol) is added drop-wise and the mixture is stirred at 0° C. for 3 hours, then at 22° C. for a further 12 hours. The reaction mixture is filtered over Dicalite and the solids washed with acetone (100 ml). The result is a solution of II in acetone.

However, preferably, an aqueous solution of VI (optionally in the form of a salt) is collected (after reduction of intermediate V) before removal of the water (via a Dean-stark trap) and the subsequent cyclization/lactone formation is performed as described below.

Example 1(a)

Bis-potassium Salt of (VI)

344 mg (2 mmol) (V) and 224 mg (4 mmol) potassium hydroxide are dissolved in 5 ml water. The solution is stirred overnight at room temperature under hydrogen atmosphere in the presence of 82 mg wet 5% rhodium on charcoal as a catalyst. The catalyst is filtered off and the filtrate, containing the bis-potassium salt of (VI), may be obtained, which may be used (e.g. directly) for the preparation of (II).

Example 1(b)

Bis-triethylamine Salt of (VI)

To a hydrogenation autoclave, 2.5 kg (14.5 mol) (V), 1 kg Raney nickel, 4.04 L (29 mol) triethylamine and 4.16 L water were loaded. The solution was stirred and heated to 120° C. under 20 bar hydrogen pressure for 23 hours. The mixture was cooled, the catalyst was filtered off and the filtrate was used as such (i.e. directly, without separation/removal of the water) for the preparation of (II).

Lactonization Procedure to Obtain Bicyclic Lactone (II)

Example 1(c)

87.7 g (0.499 mol) 2-chloro-4,6-dimethoxy-1,3,5-triazine (CDMT) and 860.3 ml acetone were added to a reaction vessel under nitrogen. The mixture was cooled to 15° C. and a 192.8 g portion of the solution prepared as in example 1(b) (i.e. bis-triethylamine salt of (VI) mixed with water, i.e. an aqueous mixture or aqueous solution), containing 0.227 mol of (VI) as its bis-triethylamine salt, was added. 52.8 g (0.522 mol) N-methylmorpholine (NMM) was added to the reactor over 3 hours (the temperature rose from 15° C. to 25° C.). The reaction mixture was then stirred for 2 hours at 15° C. The precipitate (consisting mainly of triazine byproduct) was filtered, the reactor was rinsed with 57.8 ml acetone and poured onto the filter.

Formation of Racemic Cinchonidine Salt (III), Followed by Conversion to a Single Enantiomer of Cinchonidine Salt (IV)

Example 1(d)

The main filtrate and the washing were combined and added to a reactor. To this solution, 66.8 g (0.227 mol) of cinchonidine was added at room temperature. The mixture was heated and stirred at 30° C. for 40 minutes, then cooled to 20° C. and seeded with 1.02 g cinchonidine salt (IV) (i.e. the enantiomerically pure salt). The mixture was stirred at 20-25° C. for 20 hours, filtered, and the precipitate was washed with a mixture of 11.4 ml water and 11.4 ml acetone. The crude wet product (33.6 g) was loaded into a reactor, 140.2 mL of ethanol and 5.5 mL of water were added, and the mixture was heated and stirred at 77° C. for 3 hours. The mixture was allowed to cool with stirring to 23° C. over 2 hours, then stirred 12.5 hours at 22° C. The solids were filtered and washed with 11.4 mL of ethanol, and dried under vacuum at 50° C. for 4 hours to give 26.2 g of (IV) with the following analytical characteristics: chemical purity—acid titration 99.4 w/w % and base titration 100 w/w %; chiral purity—e.r. 96.5/3.5

Lactonization Procedure to Obtain Bicyclic Lactone (II)

Example 2

735 mg of 23.7 w/w % aqueous solution of VI, bis-potassium salt (1 mmol) was diluted in 4 ml water and mixed with 728 μL of NMM (6.6 mmol). 406 mg (2.2 mmol) TCT was added and the reaction mixture was stirred overnight at room temperature before dilution to a final volume of 10 ml to give a 78 mM aqueous solution of II (yield: 78%).

Example 3

728 μL of NMM (6.6 mmol) was mixed with 4 ml water and 406 mg (2.2 mmol) TCT was added. The mixture was stirred a few minutes before adding 735 mg of 23.7 w/w % aqueous solution of VI, bis-potassium salt (1 mmol). The resulting reaction mixture was further stirred overnight at room temperature before dilution to a final volume of 10 ml to give a 57 mM aqueous solution of II (yield: 57%).

Example 4

735 mg of 23.7 w/w % aqueous solution of VI, bis-potassium salt (1 mmol) was diluted in 4 ml water and mixed with 221 μL NMM (2 mmol). 648 mg (2.2 mmol) DMTMM.$H_2O$ was added and the reaction mixture was stirred overnight at room temperature before dilution to a final volume of 10 ml to give a 54 mM aqueous solution of II (yield: 54%).

Example 5

386 mg (2.2 mmol) CDMT was dissolved in 4 ml acetone and 463 μL (4.2 mmol) NMM was added. The mixture was stirred a few minutes then 735 mg of 23.7 w/w % aqueous solution of VI, bis-potassium salt was added. The resulting mixture was further stirred overnight at room temperature before dilution to a final volume of 10 ml to give a 69 mM solution of II (yield: 69%).

Example 6

386 mg (2.2 mmol) CDMT was dissolved in 4 ml MeTHF and 463 μL (4.2 mmol) NMM was added. The mixture was stirred a few minutes then 735 mg of 23.7 w/w % aqueous solution of VI, bis-potassium salt was added. The resulting mixture was further stirred overnight at room temperature before dilution to a final volume of 10 ml to give a 54 mM solution of II (yield: 54%).

Example 7

5.66 g (32.2 mmol) CDMT was dissolved in 59 ml MeTHF. 3.7 ml (33.7 mmol) NMM was added and the mixture was stirred 1 h at 25° C. 10.0 g of 25.5 w/w % aqueous solution of VI.2NMM (14.6 mmol) was added and the resulting mixture was further stirred a few hours at 25° C. 15 ml water and 3 ml concentrated HCl were added. The mixture was stirred a few minutes, the insoluble materials were filtered off, the filtrate was decanted and the water layer was extracted with 15 ml MeTHF. The organic layers were combined and washed with 7 ml brine to give 53.1 g of 2.59 w/w % solution of II in MeTHF, which also contained 0.23 w/w % VI (yield: 60%).

Example 8

5.66 g (32.2 mmol) CDMT was dissolved in 59 ml isopropyl acetate. 3.7 ml (33.7 mmol) NMM was added and the mixture was stirred 1 h at 25° C. 10.0 g of 25.5 w/w % aqueous solution of bis N-methylmorpholine salt of VI (14.6 mmol) was added and the resulting mixture was further stirred a few hours at 25° C. 15 ml water and 3 ml concentrated HCl were added. The mixture was stirred a few minutes, the insoluble materials were filtered off, the filtrate was decanted and the water layer was extracted with 15 ml isopropyl acetate. The organic layers were combined and washed with 7 ml brine to give 56.6 g of 1.3 w/w % solution of II in isopropyl acetate that also contained 0.18 w/w % VI (yield: 32%).

Example 9

5.66 g (32.2 mmol) CDMT was dissolved in 59 ml acetone. 3.7 ml (33.7 mmol) NMM was added and the mixture was stirred 1 h at 25° C. 10.0 g of 25.5 w/w % aqueous solution of bis N-methylmorpholine salt of VI (14.6 mmol) was added and the resulting mixture was further stirred a few hours at 25° C. The insoluble materials were filtered off, 1 ml concentrated HCl was added to the filtrate and the filtrate was decanted. The organic layer was washed with 7 ml brine to give 44.4 g of 1.44 w/w % solution of II in MeTHF, which also contained 0.04 w/w % VI (yield: 28%).

Example 10

19.80 g (113 mmol) CDMT was dissolved in 205 ml MeTHF. 13 ml (118 mmol) NMM was added and the mixture was stirred at 25° C. for 2 h. 35 g of 25.5 w/w % aqueous solution of bis N-methylmorpholine salt of VI (51.3 mmol) was added and the reaction mixture was stirred overnight at 25° C. 51 ml water and 10.6 ml concentrated HCl were added and the mixture was stirred a few minutes at 25° C. The resulting solid was filtered off and the filtrate was decanted. The organic layer was washed with 51 ml water and 26 ml brine to give 181.7 g of 2.13 w/w % II solution in MeTHF (yield: 48%).

Example 11

19.80 g (113 mmol) CDMT was dissolved in 205 ml MeTHF. 13 ml (118 mmol) NMM was added and the mixture was stirred at 25° C. for 2 h. 35 g of 25.5 w/w % aqueous solution of bis N-methylmorpholine salt of VI (51.3 mmol) was mixed with 14.3 ml (102.5 mmol) triethylamine then added to the mixture of CDMT and bis N-methylmorpholine salt of VI (NMM) and the reaction mixture was stirred overnight at 25° C. 51 ml water and 19.9 ml concentrated HCl were added and the mixture was stirred a few minutes at 25° C. The resulting solid was filtered off and the filtrate was decanted. The organic layer was washed with 51 ml water and 26 ml brine to give 163.6 g of 2.56 w/w % II solution in MeTHF (yield: 52%).

Formation of Racemic Cinchonidine Salt (III), Followed by Conversion to a Single Enantiomer of Cinchonidine Salt (IV)

Example 12

To 192.8 g of an aqueous solution of lactone acid (II), 66.8 g of cinchonidine was added under stirring, and the mixture was stirred at a temperature of 20° C. to 25° C. for 10 minutes. The mixture was warmed up to 30° C. over 5 minutes, and then stirred at this temperature during 30-40 minutes. The reaction mixture was cooled to 20° C. over 5 minutes, and stirred for 10 minutes. The reaction mixture was seeded, and allowed to crystallize under slow stirring at 20° C. to 25° C. for 20 hours, after which a suspension results. The precipitate was filtered off and washed with a mixture of 11.4 ml water and 11.4 ml acetone. The result was cinchonidine salt (III) in an enantiomeric purity of e.r. 91/9. Then 33.6 g of the resulting, wet, crude product was reslurried under inert atmosphere by adding 140.2 ml ethanol with 2% MEK (methyl ethyl ketone). Thereafter stirring was started and 5.5. ml of water was added. The reaction mixture was heated to reflux at 77° C., and stirred for 3 hours at reflux. The reaction mixture was allowed to cool to 23° C. over 2 hours, and stirred at 22° C. for 12.5 hours. The resulting precipitate product was filtered off and washed with 11.4 ml ethanol 2% MEK. The solids were dried under vacuum at 50° C. during 4 hours, to yield 22.8 g of the cinchonidine salt (III) in an enantiomeric purity (i.e. (IV) as hereinbefore defined) of e.r. 97/3.

The invention claimed is:

1. A process for the preparation of a cinchonidine salt of formula (IV) comprising the steps of:
    (a) subjecting 4-oxo-1,2-cyclopentanedicarboxylic acid (V) to reduction in an aqueous environment, thus providing an aqueous solution of racemic 4-hydroxy-1,2-cyclopentanedicarboxylic acid (VI);
    (b) adding an organic solvent to the aqueous solution obtained in (a) without separation of VI from the aqueous solution;
    (c) subjecting the racemic hydroxyacid (VI) to cyclization so as to obtain an aqueous-organic solvent solution of the corresponding racemic lactone acid (II);
    (d) adding cinchonidine to the aqueous-organic solvent solution obtained in (c) so as to obtain the cinchonidine salt (III) of the lactone acid;
    (e) allowing the cinchonidine salt to crystallize so as to obtain the enantiomerically purified crystalline lactone acid cinchonidine salt (IV), the numbered formulae herein being as follows:

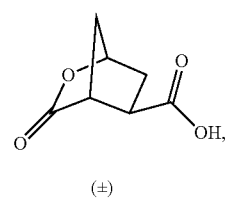

(II)

(±)

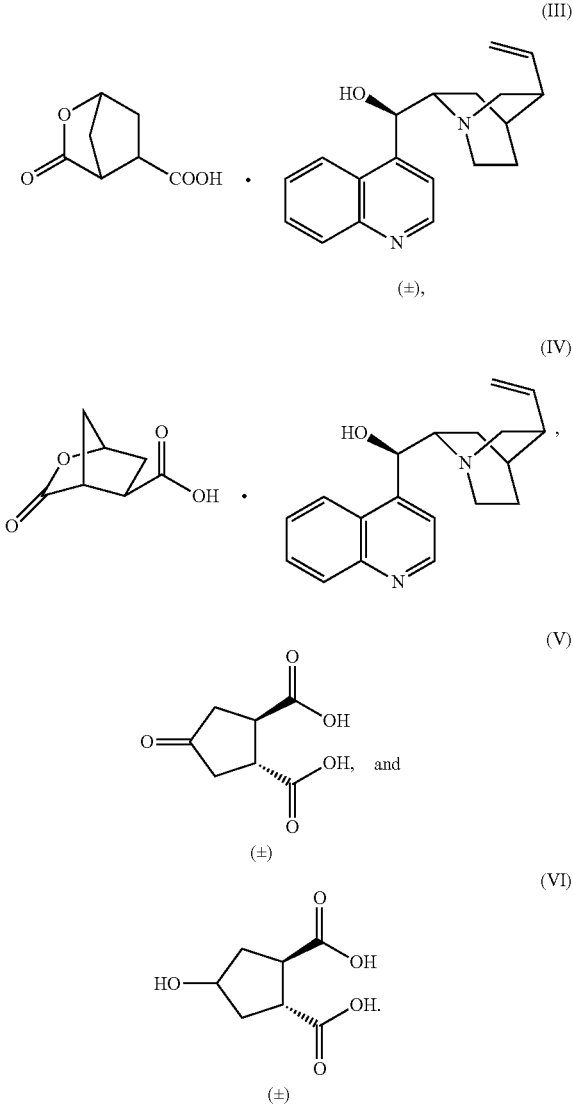

2. A process as claimed in claim 1 for the preparation of a racemic lactone of formula (II), which process comprises intramolecular cyclization of a compound of formula (VI), characterized in that the reaction is performed in the presence of water.

3. A process as claimed in claim 2, which is preceded by the reduction of racemic compound (V) to racemic compound (VI), which reduction is performed in the presence of water, and which reduction reaction is optionally proceeded by the addition of an organic solvent.

4. A process as claimed in claim 1 for the preparation of a cinchonidine salt of formula (III) or (IV), which process comprises contacting cinchonidine with racemic lactone acid (II), characterized in that the reaction is performed in the presence of water.

5. A process as claimed in claim 4, which process is proceeded by a process to prepare (III) or (IV).

6. A process according to claim 3, wherein the organic solvent is selected from the group consisting of acetone, methylethylketone (MEK), tetrahydrofuran (THF), MeTHF, CPME (cyclopentyl methyl ether), $C_{1-4}$alkyl acetate, $C_{1-4}$alkyl propionate, $C_{1-4}$alkyl butyrate or toluene.

7. A process according to claim 1 wherein the cyclization is conducted using a triazine derivative.

8. A process according to claim 7, wherein the triazine derivative is selected from the group consisting of 2,4,6-trichloro-1,3,5-triazine (TCT), chloro-dimethoxytriazine (CDMT), N-(3,5-dimethoxytriazinyl)-N-methylmorpholinium chloride (DMTMM), and dichloro-methoxytriazine (DCMT).

9. A process according to claim 1, wherein the cyclization is conducted in the presence of a tertiary amine, preferably triethylamine or N-methylmorpholine (NMM).

10. A process of claim 1, further comprising reacting the lactone acid cinchonidine salt (IV) with N-methyl-hexenamine (NMHA) (VII) in an amide-forming reaction to yield the bicyclic lactone amide (VIII), in which the lactone group is opened to yield the desired product (IX), in accordance with the following scheme:

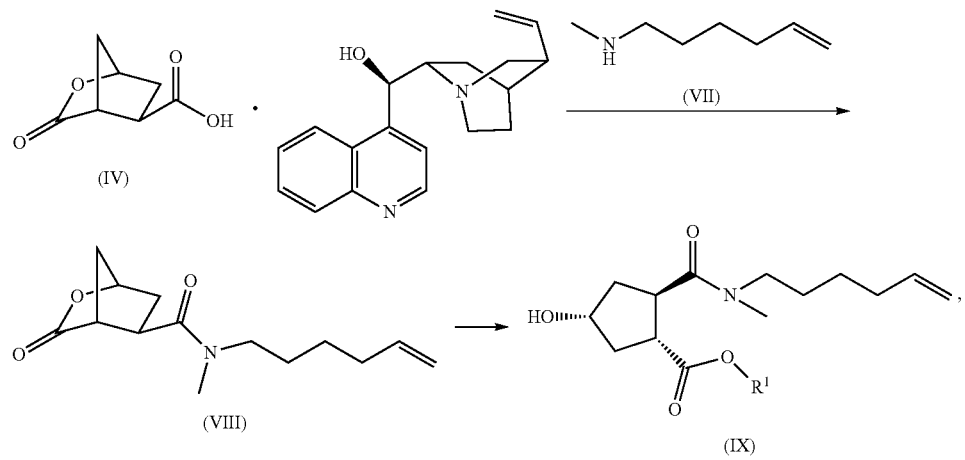

wherein $R^1$ is $C_{1-4}$alkyl.

11. A process according to claim 10, wherein $R^1$ is methyl.

12. A process of claim 10 comprising using compound (IX) as an intermediate in the synthesis of the compound of formula (I):

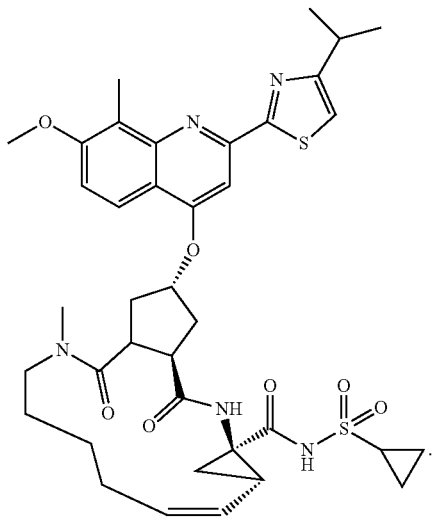 [SMILES: COc1ccc2c(O[C@H]3CC4C(=O)N(C)CCCC/C=C\[C@@H]5C[C@@]5(C(=O)NS(=O)(=O)C5CC5)NC(=O)[C@@H]4C3)cc(-c3nc(C(C)C)cs3)nc2c1C]

13. The process of claim 1, further comprising preparing compound (IX) and using compound (IX) as an intermediate in the synthesis of compound (I).

14. The process of claim 2, further comprising preparing compound (IX) and using compound (IX) as an intermediate in the synthesis of compound (I).

15. The process of claim 14, wherein compound (IV) is prepared by contacting cinchonidine with racemic lactone acid (II), in the presence of water.

16. The process of claim 14, wherein compound (IX) is by reacting the lactone acid cinchonidine salt (IV) with N-methyl-hexenamine (NMHA) (VII) in an amide-forming reaction to yield the bicyclic lactone amide (VIII), in which the lactone group is opened to yield the desired product (IX), in accordance with the following scheme:

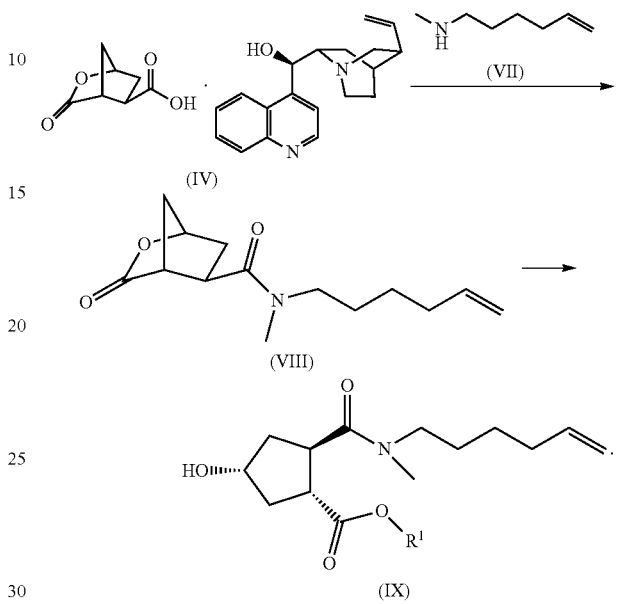

wherein $R^1$ is $C_{1-4}$ alkyl.

* * * * *